(12) United States Patent
Shin et al.

(10) Patent No.: US 9,713,460 B2
(45) Date of Patent: Jul. 25, 2017

(54) ULTRASOUND SYSTEM AND METHOD FOR PROVIDING CHANGE INFORMATION OF TARGET OBJECT

(71) Applicant: SAMSUNG MEDISON CO., LTD., Hongcheon-gun, Gangwon-Do (KR)

(72) Inventors: Dong-kuk Shin, Gangwon-do (KR); Bong-koo Seo, Gangwon-do (KR); Sung-jin Choi, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 120 days.

(21) Appl. No.: 14/267,602

(22) Filed: May 1, 2014

(65) Prior Publication Data
US 2014/0330107 A1    Nov. 6, 2014

(30) Foreign Application Priority Data

May 2, 2013    (KR) .................. 10-2013-0049427

(51) Int. Cl.
*A61B 5/00* (2006.01)
*A61B 8/08* (2006.01)
(Continued)

(52) U.S. Cl.
CPC .......... *A61B 8/5261* (2013.01); *A61B 5/0035* (2013.01); *A61B 8/5223* (2013.01); *G06T 7/0016* (2013.01); *G06T 7/248* (2017.01); *G06T 7/30* (2017.01); *G06T 2207/10132* (2013.01); *G06T 2207/10136* (2013.01); *G06T 2207/20092* (2013.01); *G06T 2207/30056* (2013.01); *G06T 2207/30096* (2013.01)

(58) Field of Classification Search
CPC ... A61B 5/0035; A61B 8/5223; A61B 8/5261; G06T 2207/10132; G06T 2207/10136
See application file for complete search history.

(56) References Cited

U.S. PATENT DOCUMENTS 6,067,371 A * 5/2000 Gouge .................. A61B 5/015
                                              374/E3.009
7,367,944 B2   5/2008 Rosemberg et al.
(Continued)

FOREIGN PATENT DOCUMENTS

DE   102008030244 A1   12/2009
EP      2574373 A1    4/2013
(Continued)

OTHER PUBLICATIONS

Lee, D., et al.: "Sensorless and Real-Time Registration Between 2D Ultrasound and Preoperative Images of the Liver", Apr. 14, 2010, XP031693601, ISBN:978-1-4244-4125-9, pp. 338-391.
(Continued)

*Primary Examiner* — Baisakhi Roy
(74) *Attorney, Agent, or Firm* — McDermott Will & Emery LLP (57) ABSTRACT

Provided are an ultrasound system and method for providing change information of a target object by performing image registration on a reference image acquired before radiofrequency ablation (RFA) and an ultrasound image acquired during the RFA and comparing the reference image and the ultrasound image that have undergone the image registration with each other.

46 Claims, 5 Drawing Sheets

(51) Int. Cl.
*G06T 7/00* (2017.01)
*G06T 7/30* (2017.01)
*G06T 7/246* (2017.01)

(56) References Cited

U.S. PATENT DOCUMENTS

| | | | |
|---|---|---|---|
| 7,871,406 B2 | 1/2011 | Nields et al. | |
| 8,155,416 B2 | 4/2012 | Nields et al. | |
| 8,226,560 B2* | 7/2012 | Arai | A61B 8/13 128/916 |
| 2006/0120581 A1* | 6/2006 | Eck | A61B 6/481 382/128 |
| 2007/0010743 A1 | 1/2007 | Arai | |
| 2007/0173720 A1* | 7/2007 | Burdette | G01S 7/52071 600/438 |
| 2008/0033240 A1 | 2/2008 | Hoffman et al. | |
| 2008/0199048 A1* | 8/2008 | Eck | G06T 7/0038 382/107 |
| 2008/0262354 A1* | 10/2008 | Yoshida | A61B 8/469 600/443 |
| 2009/0326373 A1 | 12/2009 | Boese et al. | |
| 2010/0061603 A1 | 3/2010 | Mielekamp et al. | |
| 2011/0046483 A1 | 2/2011 | Fuchs et al. | |
| 2012/0071749 A1* | 3/2012 | Xu | A61B 6/5247 600/411 |
| 2013/0237811 A1* | 9/2013 | Mihailescu | A61B 5/064 600/424 |

FOREIGN PATENT DOCUMENTS

| | | |
|---|---|---|
| JP | 2010-274043 A | 12/2010 |
| JP | 2013-005994 A | 1/2013 |
| KR | 10-2008-0068640 A | 7/2008 |
| WO | 2009-094646 A2 | 7/2009 |
| WO | 2010-057067 A2 | 5/2010 |
| WO | 2013-018003 A1 | 2/2013 |

OTHER PUBLICATIONS

Korean office Action issued in corresponding Korean Application No. 10-2013-0049427, dated Aug. 5, 2014, with English translation.
Extended European Search Report issued in corresponding European Application No. 14166594.3, dated Sep. 9, 2014.
Notice of Allowance issued in corresponding Korean Patent Application No. 10-2013-0049427, mailed on Jul. 21, 2015; with English translation.
Communication Pursuant to Article 94(3) EPC dated May 8, 2017, issued in European Application No. 14166594.3.

* cited by examiner

ULTRASOUND SYSTEM AND METHOD FOR PROVIDING CHANGE INFORMATION OF TARGET OBJECT

RELATED APPLICATIONS

This application claims the benefit of Korean Patent Application No. 10-2013-0049427, filed on May 2, 2013, in the Korean Intellectual Property Office, the disclosure of which is incorporated herein in its entirety by reference.

BACKGROUND

1. Field

One or more embodiments of the present invention relate to ultrasound systems, and more particularly, to ultrasound systems and methods for providing change information of a target object that has undergone radiofrequency ablation (RFA).

2. Description of the Related Art

When tumors occur in a target object (e.g., the liver) inside a living body, the tumors are typically removed by non-surgical method or surgical treatment. Since the surgical treatment usually removes a tumor by incising a surface of a living body, the cut surface is so wide as to leave a scar thereon and takes a long time to heal. Furthermore, the tumor is likely to recur, and in this case the tumor has to be removed with surgery again, thereby causing pain in a living body and considerable economic burden and health risk.

Recently, non-surgical techniques have been commonly used to remove tumors. Examples of non-surgical techniques may include transarterial chemoinfusion (TACE), percutaneous ethanol injection (PEI), systemic chemotherapy, and local ablation therapy. Among these, the local ablation therapy is known as the most effective technique for providing short-term treatment and improving a long-term survival rate. Some examples of the local ablation therapy are RFA, microwave endometrial ablation (MEA), and laser ablation. The RFA is the most effective treatment modality.

The RFA is a treatment technique that destroys only a tumor by application of RF-generated heat without incision to thereby cause necrosis. The RFA involves inserting a needle-tip electrode into a tumor within a living body, supplying RF from an RF generator to the needle-tip electrode, and burning the tumor with RF-generated heat to ablate it.

A conventional technique provides information about a progress of an RFA process by setting markers on ultrasound images obtained before and after the RFA process or superimposing ultrasound images obtained before and after the RFA process. Thus, the conventional technique has drawbacks in that it is difficult to consistently observe the progress of RFA from different planes and positions during RFA and accurately observe it due to gas bubbles created during the RFA.

SUMMARY

One or more embodiments of the present invention include an ultrasound system and method for providing change information of a target object by performing image registration on a reference image acquired before radiofrequency ablation (RFA) and an ultrasound image acquired during the RFA and comparing the reference image and the ultrasound image that have undergone the image registration with each other.

Additional aspects will be set forth in part in the description which follows and, in part, will be apparent from the description, or may be learned by practice of the presented embodiments.

According to one or more embodiments of the present invention, an ultrasound system includes: a storage unit that stores image data of a living body containing a target object, which is acquired before undergoing RFA; an ultrasound probe that transmits an ultrasound signal to the living body during the RFA and receives an ultrasound echo signal reflected from the living body to create a reception signal; an ultrasound data acquisition unit configured to acquire ultrasound data by using the reception signal; and a processing unit that produces a reference image by using the image data and an ultrasound image by using the ultrasound data, performs image registration between the reference image and the ultrasound image, compares the reference image and the ultrasound image that have undergone the image registration with each other, and produces change information indicative of a change in the target object.

According to one or more embodiments of the present invention, a method of providing change information of a target object includes: transmitting an ultrasound signal to a living body containing the target object during radiofrequency ablation (RFA) and receiving an ultrasound echo signal reflected from the living body to acquire ultrasound data, through an ultrasound probe; extracting image data of the living body acquired before undergoing the RFA from a storage unit and producing a reference image; producing an ultrasound image by using the ultrasound data; performing image registration between the reference image and the ultrasound image; and comparing the reference image and the ultrasound image that have undergone the image registration with each other and producing the change information indicative of a change in the target object.

The ultrasound system and method for providing change information of a target object allow a user to view a size of a tumor before RFA, a targeted range of the RFA, and real-time progress status of the RFA, thereby achieving real-time monitoring of the progress of the RFA from various angles and positions during RFA.

The ultrasound systems and method are adapted to monitor a status corresponding to a portion of an image that is momentarily blurred due to gas bubbles through accumulation of images.

The ultrasound system and method may also be adapted to store the progress of a RFA process, thereby enabling a review of the progress.

The ultrasound system and method are also adapted to simultaneously observe the progress of an RFA process by using various modalities such as MRI, CT, ultrasound, and PET-CT.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Embodiment 1

Figure 1:
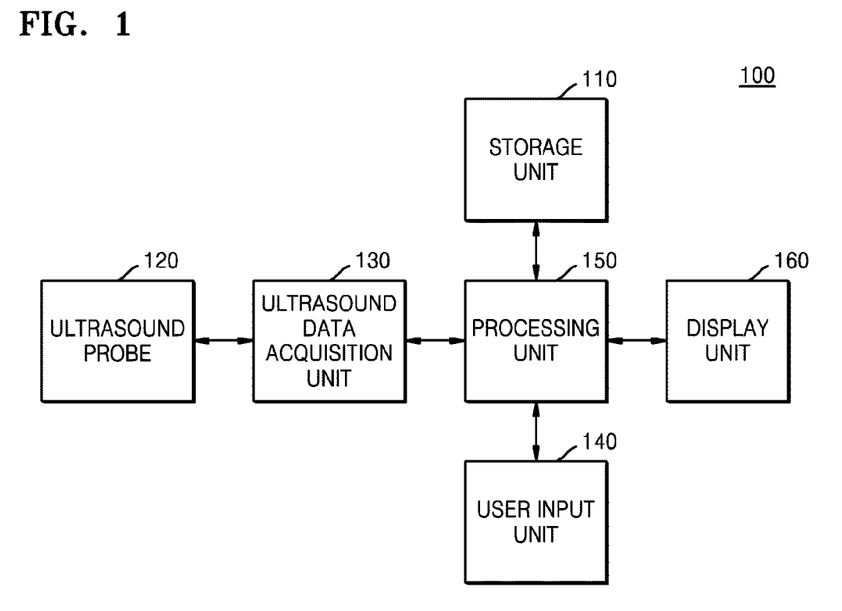
FIG. 1 is a schematic block diagram showing a configuration of an ultrasound system according to an exemplary embodiment of the present invention.

FIG. 1 is a schematic block diagram showing a configuration of an ultrasound system 100 according to an exemplary embodiment of the present invention. Referring to FIG. 1, the ultrasound system 100 includes a storage unit 110, an ultrasound probe 120, an ultrasound data acquisition unit 130, a user input unit 140, a processing unit 150, and a display unit 160.

The storage unit 110 stores image data corresponding to an image of a living body including a target object (e.g., a tumor). According to the present embodiment, the image data corresponds to an image of a living body obtained before radiofrequency ablation (RFA). Furthermore, the image data may be two-dimensional (2D) or three-dimensional (3D) data. The image data may include magnetic resonance imaging (MRI) data, computed tomography (CT) data, ultrasound data, and positron emission tomography (PET)-CT data. The storage unit 110 may include a hard disk, a non-volatile memory, Compact Disc-Read Only Memory (CD-ROM), and Digital Versatile Disc (DVD)-ROM.

The ultrasound probe 120 includes a plurality of transducer elements (not shown) that convert electrical signals into ultrasound signals, and vice versa. The ultrasound probe 120 is configured to transmit an ultrasound signal to a living body and receive an ultrasound echo signal reflected from the living body to generate an electrical signal (hereinafter, referred to as a "reception signal"). The reception signal is an analog signal. The ultrasound probe 120 includes a 3D probe, a 2D array probe, a convex probe, and a linear probe.

The ultrasound data acquisition unit 130 controls transmission of an ultrasound signal. The ultrasound data acquisition unit 130 also acquires ultrasound data corresponding to an ultrasound image of a living body by using a reception signal provided by the ultrasound probe 120. The ultrasound data acquisition unit 130 may be realized by an Application Specific Integrated Circuit (ASIC) or a processor including a central processing unit (CPU), a microprocessor, and a graphics processing unit (GPU).

Figure 2:
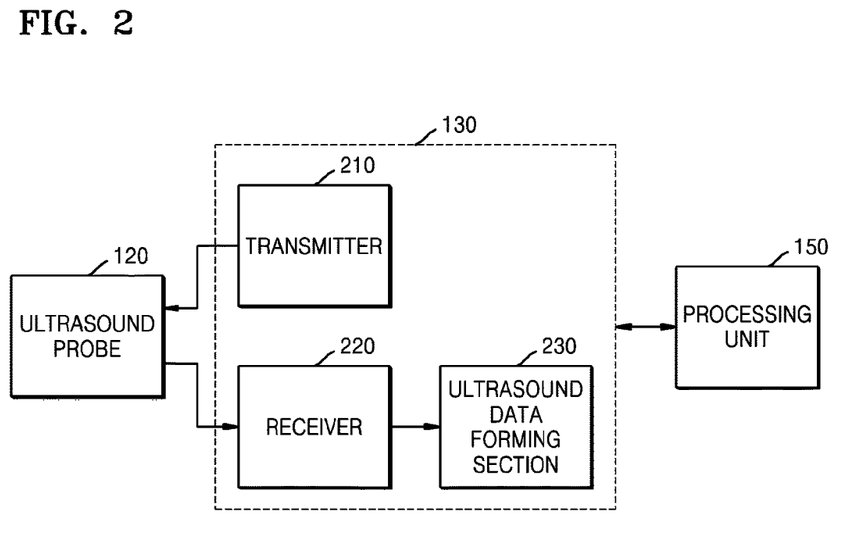
FIG. 2 is a block diagram showing a configuration of an ultrasound data acquisition unit in the ultrasound system of FIG. 1, according to an exemplary diagram of the present invention.

FIG. 2 is a block diagram showing a configuration of the ultrasound data acquisition unit 130 in the ultrasound system of FIG. 1, according to an exemplary diagram of the present invention. Referring to FIG. 2, the ultrasound data acquisition unit 130 includes a transmitter 210, a receiver 220, and an ultrasound data forming section 230.

The transmitter 210 controls the transmission of an ultrasound signal. The transmitter 210 also produces an electrical signal (hereinafter, referred to as a "transmission signal") that is used to obtain an ultrasound image in consideration of the transducer elements. In the present embodiment, the transmitter 210 creates a transmission signal that is used to obtain each of a plurality of ultrasound images during RFA.

In one embodiment, the transmitter 210 creates a transmission signal (hereinafter, referred to as a "first transmission signal") that is used to obtain each of a plurality of 2D images of a living body during RFA. The ultrasound probe 120 then converts the first transmission signal received from the transmitter 210 into an ultrasound signal, transmits the ultrasound signal to the living body, and receives an ultrasound echo signal reflected from the living body to create a reception signal (hereinafter, referred to as a "first reception signal").

Figure 3:
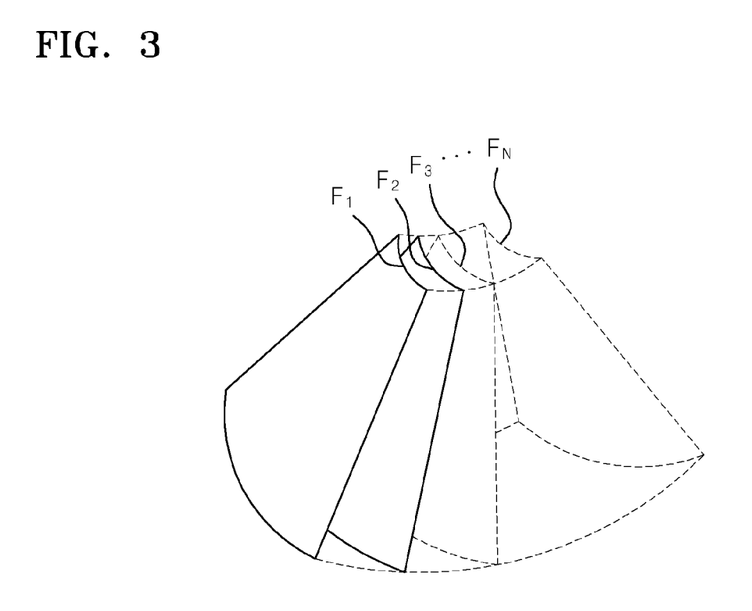
FIG. 3 is an exemplary diagram illustrating a plurality of frames.

In another embodiment, as shown in FIG. 3, during RFA, the transmitter 210 creates a transmission signal (hereinafter, referred to as a "second transmission signal") that is used to obtain each of a plurality of 3D ultrasound images of a living body, i.e., a plurality of frames $F_i$ ($1 \leq i \leq N$) corresponding to the plurality of 3D ultrasound images. The ultrasound probe 120 then converts the first transmission signal received from the transmitter 210 into an ultrasound signal, transmits the ultrasound signal to the living body, and receives an ultrasound echo signal reflected from the living body to create a reception signal (hereinafter, referred to as a "second reception signal").

The receiver 220 performs analog-to-digital conversion on the reception signal provided by the ultrasound probe 120 to produce a digital signal. The receiver 220 also performs reception beamforming on the digital signal in consideration of positions of the transducer elements to create a focused reception signal. Since the reception beamforming may be performed by using various known methods, a detailed description thereof is omitted here. In the present embodiment, during RFA, the receiver 220 performs analog-to-digital conversion on the reception signal received from the ultrasound probe 120 to produce a digital signal and carries out reception beamforming on the digital signal to create a focused reception signal.

In one embodiment, the receiver 220 performs analog-to-digital conversion on a first reception signal provided by the ultrasound probe 120 to produce a digital signal (hereinafter, referred to as a "first digital signal"). The receiver 220 may also perform reception beamforming on the first digital signal in consideration of the transducer elements to create a focused reception signal (hereinafter, referred to as a "first focused reception signal").

In another embodiment, the receiver 220 performs analog-to-digital conversion on a first reception signal provided by the ultrasound probe 120 to produce a digital signal (hereinafter, referred to as a "second digital signal"). The receiver 220 may also perform reception beamforming on the second digital signal in consideration of the transducer elements to create a focused reception signal (hereinafter, referred to as a "second focused reception signal").

The ultrasound data forming section 230 creates ultrasound data corresponding to an ultrasound image by using the focused reception signal provided by the receiver 220. The ultrasound data includes RF data, but is not limited thereto. The ultrasound data may be stored in the storage unit 110. The ultrasound data forming section 230 may also perform various signal processings, such as gain control, needed to form ultrasound data, on the focused reception signal. In the present embodiment, during RFA, the ultrasound data forming section 230 generates ultrasound data by using the focused reception signal received from the receiver 220.

In one embodiment, the ultrasound data forming section 230 generates ultrasound data (hereinafter, referred to as 'first ultrasound data') corresponding to a 2D ultrasound image obtained during RFA, by using the first focused reception signal provided by the receiver 220.

In another embodiment, the ultrasound data forming section 230 generates ultrasound data (hereinafter, referred to as 'second ultrasound data') corresponding to a 3D ultrasound image obtained during RFA, by using the second focused reception signal provided by the receiver 220.

Although the ultrasound data acquisition unit 130 has been described to acquire ultrasound data corresponding to an ultrasound image based on a reception signal provided by the ultrasound probe 120, the ultrasound data acquisition unit 130 may acquire ultrasound data from an external device (not shown) connected to the ultrasound system 100 in a wired or wireless manner.

Referring back to FIG. 1, the user input unit 140 receives user input information. In the present embodiment, the user input information includes information needed for setting a region of interest (ROI). That is, the information needed for setting an ROI may contain a size and a location of the ROI. The ROI may include a 2D or 3D ROI. However, the user input information is not limited thereto. The user input information may be stored in the storage unit 110. The user input unit 140 includes a control panel, a track ball, a touch screen, a keyboard, and a mouse.

The processing unit 150 is connected to the storage unit 110, the ultrasound probe 120, the ultrasound data acquisition unit 130, the user input unit 140, and the display unit 160 and controls operations of the storage unit 110, the ultrasound probe 120, the ultrasound data acquisition unit 130, the user input unit 140, and the display unit 160. The processing unit 150 may be a processor including a CPU, a microprocessor and a GPU, or an ASIC.

Figure 4:
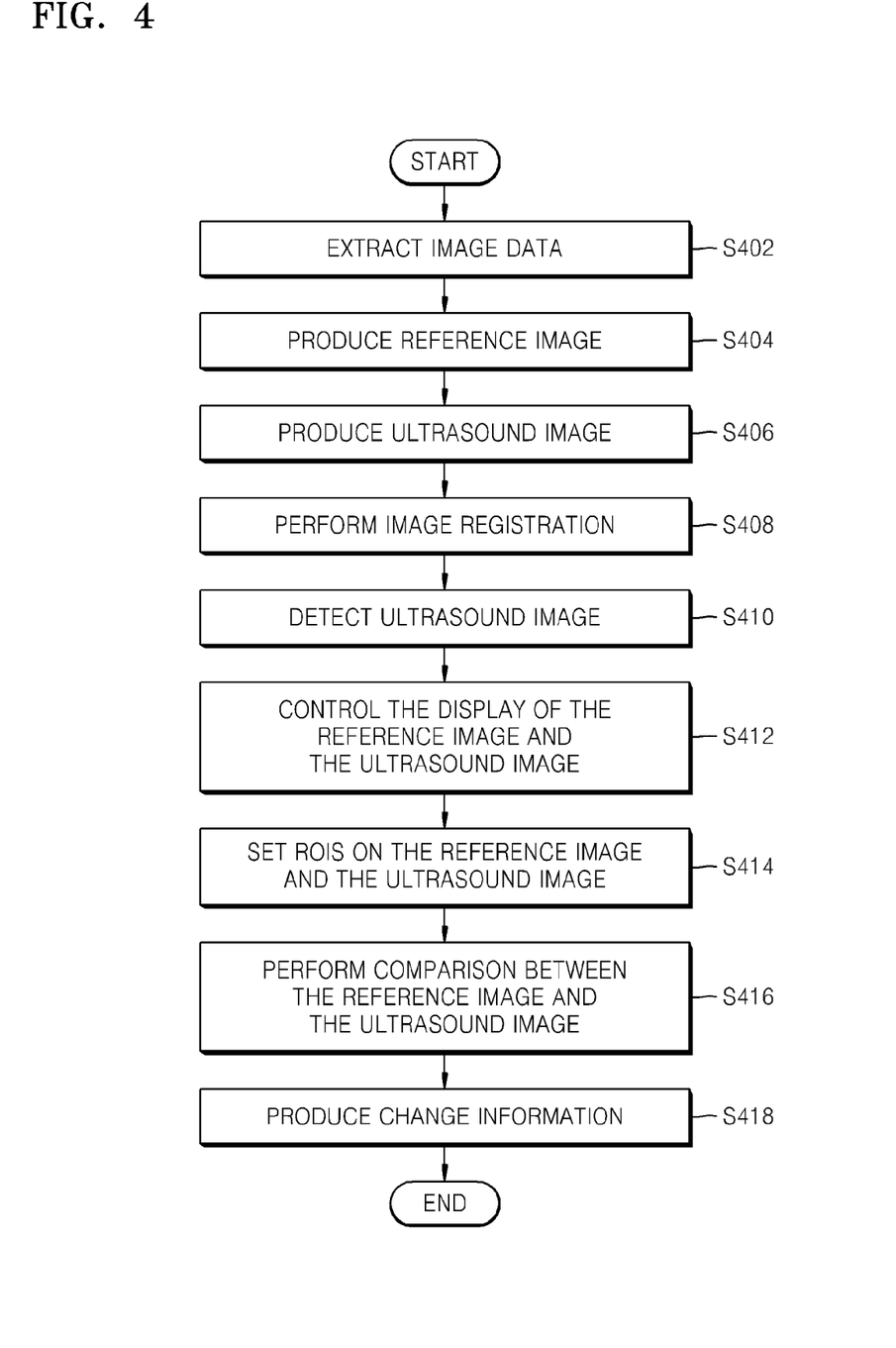
FIG. 4 is a flowchart of a process of generating change information associated with radiofrequency ablation (RFA) according to an exemplary embodiment of the present invention.

FIG. 4 is a flowchart of a process of generating change information associated with RFA according to an exemplary embodiment of the present invention. Referring to FIGS. 1 and 4, the processing unit 150 extracts image data from the storage unit 110 (S402) and produces an image (hereinafter, referred to as a "reference image") of a living body before undergoing RFA by using the extracted image data (S404). The reference image may include an MRI image, a CT image, an ultrasound image, and a PET-CT image. The reference image may also include 2D and 3D images.

Upon receipt of ultrasound data from the ultrasound data acquisition unit 130, the processing unit 150 produces an ultrasound image $UI_i$ ($i≥1$) of a living body that is undergoing the RFA by using the ultrasound data (S406). The ultrasound image $UI_i$ includes a 2D or 3D ultrasound image.

The processing unit 150 performs image registration between the reference image and the ultrasound image $UI_i$ (S408). Since the image registration may be performed by using various known methods, a detailed description thereof is omitted here.

The processing unit 150 then compares the reference image with the ultrasound image $UI_i$ and detects an ultrasound image for producing change information about a target object (S410).

In one embodiment, the processing unit 150 compares values (i.e., brightness values) of pixels in the reference image with values (i.e., brightness values) of corresponding pixels in the ultrasound image $UI_i$, and if a brightness value difference between the reference image and the ultrasound image $UI_i$ exceeds a preset threshold value, the processing unit 150 determines that the brightness values of pixels in the ultrasound image $UI_i$ have undergone a rapid change due to gas bubbles generated during RFA and then removes the ultrasound image $UI_i$. On the other hand, if the brightness value difference between the reference image and the ultrasound image $UI_i$ is less than or equal to the preset threshold value, the processing unit 150 sets the ultrasound image $UI_i$ as an ultrasound image for producing change information about a target object.

In another embodiment, the processing unit 150 compares values (i.e., brightness values) of voxels in the reference image with values (i.e., brightness values) of corresponding voxels in the ultrasound image $UI_i$, and if a brightness value difference between the reference image and the ultrasound image $UI_i$ exceeds a preset threshold value, the processing unit 150 determines that the brightness values of voxels in the ultrasound image $UI_i$ has undergone a rapid change due to gas bubbles generated during RFA and removes the ultrasound image $UI_i$. On the other hand, if the brightness value difference between the reference image and the ultrasound image $UI_i$ is less than or equal to the preset threshold value, the processing unit 150 sets the ultrasound image $UI_i$ as an ultrasound image for producing change information about a target object.

The processing unit 150 controls the display of the reference image and the ultrasound image $UI_i$ that have undergone image registration (S412). In one embodiment, the processing unit 150 controls the display unit 160 to display the reference image on one side of the display unit 160 while displaying the ultrasound image $UI_i$ on the other side thereof. In another embodiment, the processing unit 150 controls the display unit 160 to display the reference image and the ultrasound image $UI_i$ superimposed on top of each other.

The processing unit 150 sets ROIs on the reference image and the ultrasound image $UI_i$ that have been image registered, based on input information provided by the user input unit 140 (S414).

In one embodiment, the processing unit 150 sets a point on the reference image based on input information that is used for setting a point on a target object in the reference image as an ROI. The processing unit 150 then performs edge detection on the reference image based on the set point to detect an edge of the target object. The edge may be detected using an edge mask such as a Sobel mask, a Prewitt mask, a Robert mask, and a Canny mask. Alternatively, the edge may be detected from a difference between eigen values using a structure tensor. The processing unit 150 then sets an ROI corresponding to the target object on the reference image by using the detected edge. The processing unit 150 also sets a point on the ultrasound image $UI_i$ based on the point set on the reference image. The processing unit 150 then performs edge detection on the ultrasound image $UI_i$ based on the set point to detect an edge of the target object. Thereafter, the processing unit 150 sets an ROI corresponding to the target object on the ultrasound image $UI_i$ by using the detected edge.

In another embodiment, the processing unit 150 sets an ROI on the reference image based on input information that is used for setting an edge region of a target object in the reference image as an ROI. The processing unit 150 then performs edge detection on the ultrasound image $UI_i$ that has been image registered to the reference image, based on the ROI set on the reference image, to detect an edge of the target object. The processing unit 150 sets an ROI corresponding to the target object on the ultrasound image $UI_i$ by the detected edge.

The processing unit 150 performs image comparison based on the set ROIs (S416). The image comparison may be performed using a differential image, an intensity change, a texture change, signal phase, or signal attenuation. In one embodiment, the processing unit 150 performs image comparison between a current ultrasound image and the reference image. In another embodiment, the processor compares a current ultrasound image with a previous ultrasound image. In another embodiment, the processing unit 150 performs image comparison between a current ultrasound image and each of a predetermined number of previous ultrasound images. In another embodiment, the processing unit 150 performs image comparison among a reference image, a previous ultrasound image, and a current ultrasound image. In another embodiment, the processing unit 150 may perform image comparison among a reference image, a predetermined number of previous ultrasound images, and a current ultrasound image.

The processing unit 150 produces change information indicative of a change in a size of a target object (S418). The change information may be stored in the storage unit 110.

In one embodiment, the processing unit 150 produces change information including an ROI corresponding to a target object in a reference image and an ROI corresponding to a target object in a current ultrasound image. The ROI corresponding to the target object in the reference image may have the same color as or a different color than the ROI corresponding to the target object in the current ultrasound image. Alternatively, the ROI corresponding to the target object in the reference image may have the same shape as or a different shape than the ROI corresponding to the target object in the current ultrasound image.

In another embodiment, the processing unit 150 produces change information including an ROI corresponding to a target object in a reference image, an ROI corresponding to a target object in a current ultrasound image, and information about a difference in size of a target object due to RFA. The ROI corresponding to the target object in the reference image may have the same color as or a different color than the ROI corresponding to the target object in the current ultrasound image. Alternatively, the ROI corresponding to the target object in the reference image may have the same shape as or a different shape than the ROI corresponding to the target object in the current ultrasound image. The information about a difference in size of the target object may be represented as a number or graph.

In another embodiment, the processing unit 150 produces change information including an ROI corresponding to a target object in a reference image, an ROI corresponding to a target object in a previous ultrasound image, an ROI corresponding to a target object in a current ultrasound image, and information about a difference in size of a target object due to RFA. The ROI corresponding to the target object in the reference image, the ROI corresponding to the target object in the previous ultrasound image, and the ROI corresponding to the target object in the current ultrasound image may have the same color as or different colors than one another. Alternatively, the ROI corresponding to the target object in the reference image, the ROI corresponding to the target object in the previous ultrasound image, and the ROI corresponding to the target object in the current ultrasound image may have the same shape as or different shapes than one another. The information about a difference in size of the target object may be represented as a number or graph.

In another embodiment, the processing unit 150 produces change information including an ROI corresponding to a target object in a reference image, an ROI corresponding to a target object in each of a predetermined number of previous ultrasound images, an ROI corresponding to a target object in a current ultrasound image, and information about a difference in size of a target object due to RFA. The ROI corresponding to the target object in the reference image, the ROI corresponding to the target object in each of the predetermined number of previous ultrasound images, and the ROI corresponding to the target object in the current ultrasound image may have the same color as or different colors from one another. Alternatively, the ROI corresponding to the target object in the reference image, the ROI corresponding to the target object in each of the predetermined number of previous ultrasound images, and the ROI corresponding to the target object in the current ultrasound image may have the same shape as or different shapes from one another. The information about a difference in size of the target object may be represented as a number or graph.

In another embodiment, the processing unit 150 produces change information including an ROI corresponding to a target object in a reference image, an ROI corresponding to a target object in a current ultrasound image, and a marker (e.g., an arrow) for indicating a portion that is subjected to RFA in the current ultrasound image.

Selectively, the processing unit 150 compares a change (hereinafter, referred to as a 'first size change') in size of a target object in the reference image and in a previous ultrasound image $UI_{i-1}$ with a change (hereinafter, referred to as a 'second size change') in size of a target object in the reference image and in the current ultrasound image $UI_i$, and if a difference between the first and second size changes exceeds a preset threshold value, the processing unit 150 determines that an error occurs in the current ultrasound image $UI_i$ and removes the current ultrasound image $UI_i$ so as not to perform the above-described process.

Referring back to FIG. 1, the display unit 160 displays a reference image, an ultrasound image, and change information, all of which are generated by the processing unit 150. Examples of the display unit 160 may include a liquid crystal display (LCD), a light-emitting diode (LED) display, and an organic LED (OLED) display.

Selectively, although it is described above that the ultrasound data acquisition unit 130 and the processing unit 150 are realized as separate processors, they may be combined into a single processor.

Embodiment 2

Figure 5:
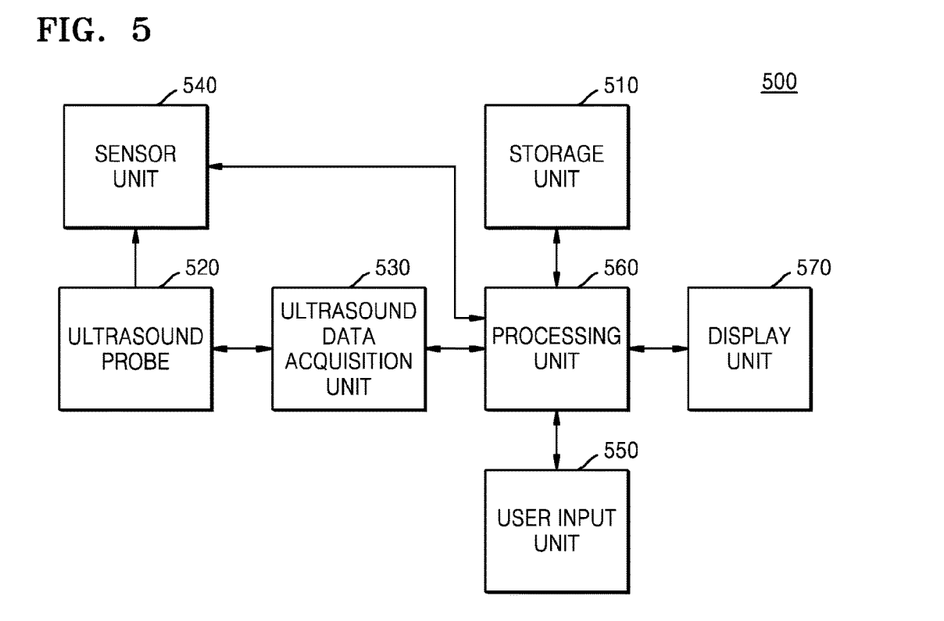
FIG. 5 is a block diagram showing a configuration of an ultrasound system according to another exemplary embodiment of the present invention.

FIG. 5 is a block diagram showing a configuration of an ultrasound system 500 according to another exemplary embodiment of the present invention. Referring to FIG. 5, the ultrasound system 500 according to the present embodiment includes a storage unit 510, an ultrasound probe 520, an ultrasound data acquisition unit 530, a sensor unit 540, a user input unit 550, a processing unit 560, and a display unit 570.

The storage unit 510 stores image data corresponding to an image of a living body. Since the storage unit 560 has the same configuration and function as those of the storage unit 110 in FIG. 1, a detailed description thereof is omitted here.

The ultrasound probe 520 includes a plurality of transducer elements (not shown) that convert electrical signals into ultrasound signals, and vice versa. The ultrasound probe 520 is configured to transmit an ultrasound signal to a living body and receive an ultrasound echo signal reflected from the living body to generate a reception signal. The reception signal is an analog signal. In the present embodiment, the ultrasound probe 520 includes a freehand type probe.

The ultrasound data acquisition unit 530 controls transmission of an ultrasound signal. The ultrasound data acquisition unit 130 also acquires ultrasound data corresponding to an ultrasound image of a living body by using a reception signal provided by the ultrasound probe 520. The ultrasound data acquisition unit 130 may be realized by an ASIC or a processor including a CPU, a microprocessor, and a GPU.

Figure 6:
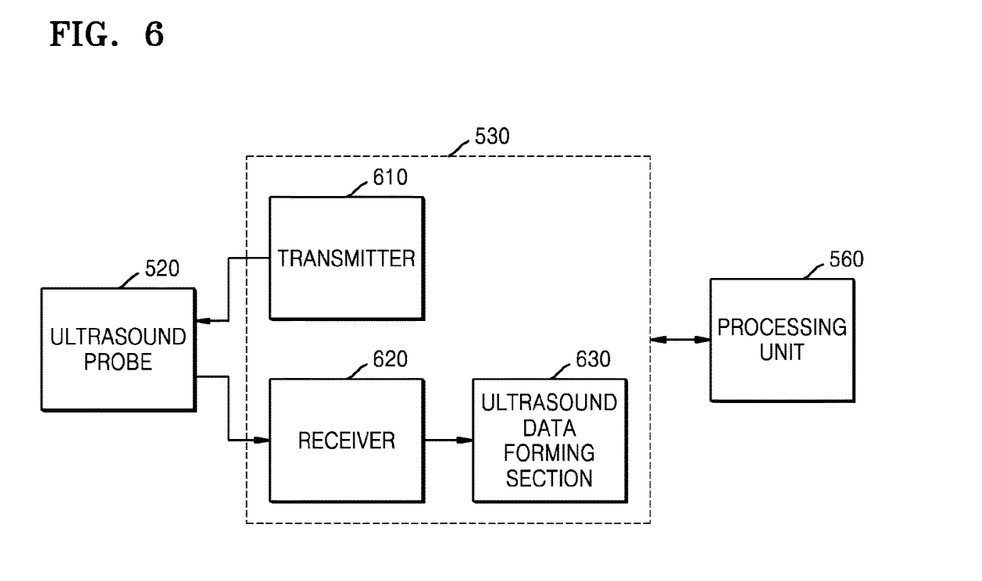
FIG. 6 is a block diagram showing a configuration of an ultrasound data acquisition unit in the ultrasound system of FIG. 5, according to an exemplary diagram of the present invention.

FIG. 6 is a block diagram showing a configuration of the ultrasound data acquisition unit 530 in the ultrasound system 500, according to an exemplary diagram of the present invention. Referring to FIG. 6, the ultrasound data acquisition unit 530 includes a transmitter 610, a receiver 620, and an ultrasound data forming section 630.

The transmitter 610 controls the transmission of an ultrasound signal. The transmitter 610 also produces a transmission signal that is used to obtain an ultrasound image in consideration of the transducer elements. In the present embodiment, the transmitter 610 creates a transmission signal that is used to obtain each of a plurality of 3D ultrasound images during RFA.

The receiver 620 performs analog-to-digital conversion on a reception signal provided by the ultrasound probe 520 to produce a digital signal. The receiver 620 also performs reception beamforming on the digital signal in consideration of positions of the transducer elements to create a focused reception signal. In the present embodiment, during RFA, the receiver 620 performs analog-to-digital conversion on the reception signal received from the ultrasound probe 520 to produce a digital signal and carries out reception beamforming on the digital signal to create a focused reception signal.

The ultrasound data forming section 630 creates ultrasound data corresponding to an ultrasound image by using the focused reception signal provided by the receiver 620. The ultrasound data includes RF data, but is not limited thereto. The ultrasound data forming section 630 may also perform various signal processings, such as gain control, needed to form ultrasound data, on the focused reception signal. In the present embodiment, during RFA, the ultrasound data forming section 630 generates ultrasound data corresponding to a 3D ultrasound image by using the focused reception signal received from the receiver 620.

Referring back to FIG. 5, a sensor unit 540 senses a 3D position (orientation) of the ultrasound probe 520 and produces position information corresponding to the sensed 3D position. According to the present embodiment, the sensor unit 540 senses a 3D position (orientation) of the ultrasound probe 520 based on a 3D position of a living body that will be subjected to RFA and produces position information corresponding to the sensed 3D position. The sensor unit 540 may be located so as to sense the 3D position of the ultrasound probe 520. For example, the sensor unit 540 may be disposed on one side of an exterior or interior surface of the ultrasound probe 520. The sensor unit 540 may be any device for sensing a 3D position of the ultrasound probe 520, such as an angular velocity sensor, a magnetic sensor, an acceleration sensor, a gravity sensor, and a gyro sensor.

The user input unit 550 receives user input information. In the present embodiment, the user input information includes information needed for setting a 3D ROI. That is, the information needed for setting a 3D ROI may contain a size and a location of the 3D ROI. However, the user input information is not limited thereto. The user input information may be stored in the storage unit 510. The user input unit 140 includes a control panel, a track ball, a touch screen, a keyboard, and a mouse.

The processing unit 560 is connected to the storage unit 510, the ultrasound probe 520, the ultrasound data acquisition unit 530, the sensor unit 540, the user input unit 560, and the display unit 570 and controls operations of the storage unit 510, the ultrasound probe 520, the ultrasound data acquisition unit 530, the sensor unit 540, the user input unit 550, and the display unit 570. The processing unit 560 include a processor including a CPU, a microprocessor and a GPU, or an ASIC.

Figure 7:
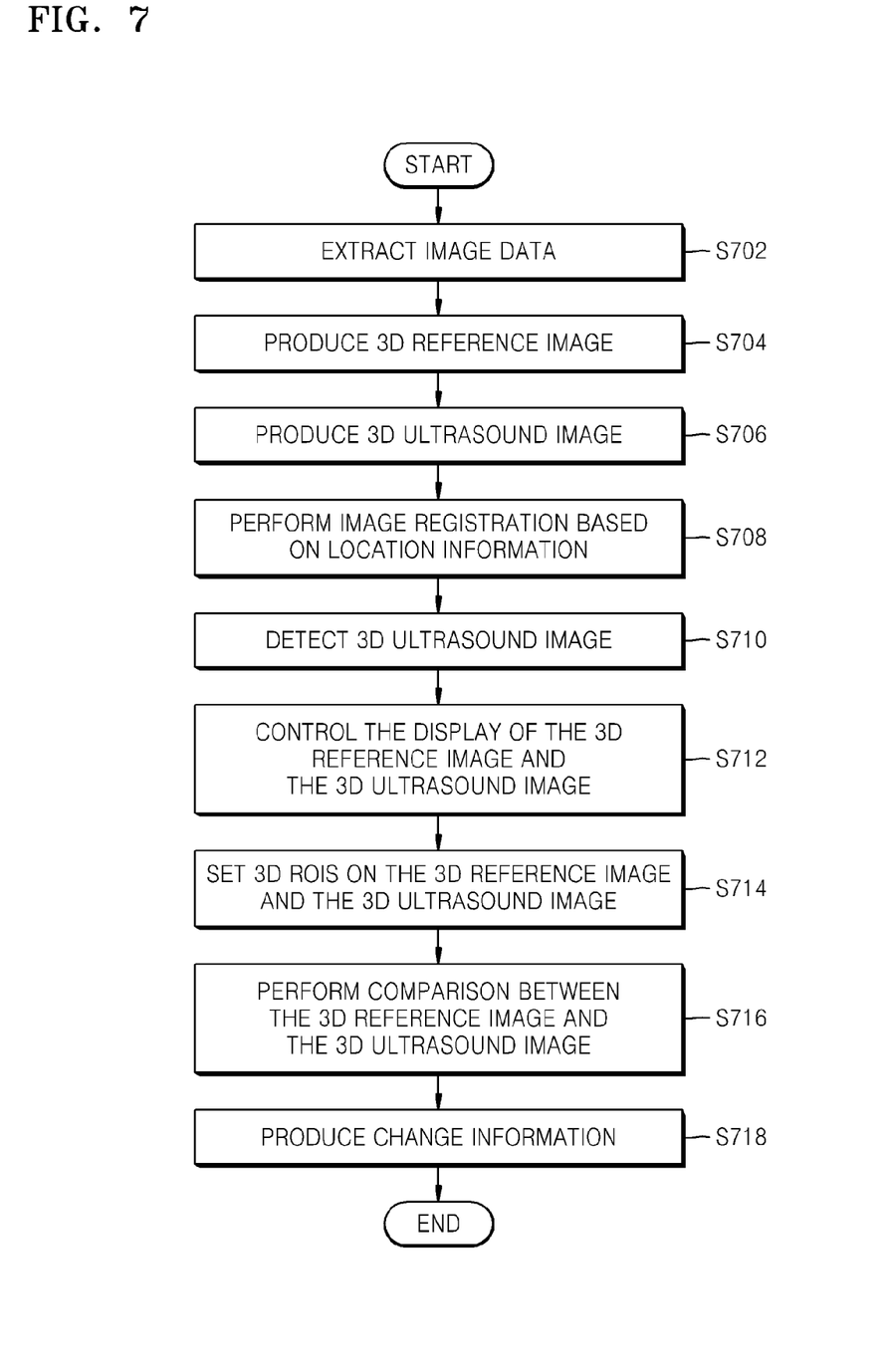
FIG. 7 is a flowchart of a process of generating change information of an object associated with RFA according to another exemplary embodiment of the present invention.

FIG. 7 is a flowchart of a process of generating change information of an object associated with RFA according to another exemplary embodiment of the present invention. Referring to FIGS. 5 and 7, the processing unit 560 extracts image data from the storage unit 510 (S702) and produces a 3D reference image of a living body before undergoing RFA by using the extracted image data (S704). The 3D reference image has 3D position information (geometric information) obtained based on a 3D position of a living body that will be subjected to RFA. The 3D reference image includes an MRI image, a CT image, an ultrasound image, and a PET-CT image.

Upon receipt of ultrasound data from the ultrasound data acquisition unit 530, the processing unit 560 produces a 3D ultrasound image $UI_i$ ($i \geq 1$) of a living body that is undergoing the RFA by using the ultrasound data (S706).

The processing unit 560 performs image registration between the 3D reference image and the 3D ultrasound image $UI_i$ based on position information of the 3D reference image and position information provided by the sensor unit 540 (S708). Since the image registration may be performed by using various known methods, a detailed description thereof is omitted here.

The processing unit 560 then compares the 3D reference image with the 3D ultrasound image $UI_i$ and detects a 3D ultrasound image for producing change information about a target object (S710).

The processing unit 560 controls the display of the 3D reference image and the 3D ultrasound image $UI_i$ that have undergone image registration (S712). The processing unit 560 sets 3D ROIs on the 3D reference image and the 3D ultrasound image $UI_i$ that have been image registered, based on input information provided by the user input unit 550 (S714). The processing unit 560 performs comparison between the 3D reference image and the 3D ultrasound image $UI_i$ that have been image registered, based on the set 3D ROIs (S716). Thereafter, the processing unit 560 produces change information indicative of a change in a size of a target object (S718). Since the operations S710 through S718 of the method according to the present embodiment are performed in a similar manner to the operations S410 through S418 of the method according to Embodiment 1, a detailed description thereof is omitted here.

Referring back to FIG. 5, the display unit 570 displays a 3D reference image, a 3D ultrasound image and change information, all of which are generated by the processing unit 560. Examples of the display unit 570 may include an LCD, an LED display, and an OLED display.

Selectively, although it is described above that the ultrasound data acquisition unit 530 and the processing unit 560 are realized as separate processors, they may be combined into a single processor.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. An ultrasound system comprising:
a storage that stores image data of a living body containing a target object, which is acquired before undergoing radiofrequency ablation (RFA);
an ultrasound probe that transmits an ultrasound signal to the living body during the RFA and receives an ultrasound echo signal reflected from the living body to create a reception signal;
an ultrasound data acquisitor configured to acquire ultrasound data by using the reception signal;
a sensor configured to detect a three-dimensional (3D) position of the ultrasound probe and create a first 3D position information of the ultrasound probe; and
a processor that produces a reference image which has a second 3D position information obtained based on a 3D position of a living body by using the image data and an ultrasound image by using the ultrasound data, performs image registration between the reference image and the ultrasound image based on the first 3D position information and the second 3D position information, compares the reference image and the ultrasound image that have undergone the image registration with each other, and produces change information indicative of a change in the target object,
wherein the processor further produces a first change information about the target object comparing the reference image and a previous ultrasound image, produces a second change information about the target object comparing the reference image and a current ultrasound image, and compares the first change information with the second change information to determine that an error occurs in the current ultrasound image, and
wherein the processor further detects a first size change in size of the target object in the reference image and in a previous ultrasound image, detects a second size change in size of the target object in the reference image and in a current ultrasound image, and compares the first size change with the second size change to determine that an error occurs in the current ultrasound image if a difference between the first and second size changes exceeds a preset threshold value and removes the current ultrasound image.

2. The ultrasound system of claim 1, wherein the image data includes at least one of magnetic resonance imaging (MRI) data, computed tomography (CT) data, ultrasound data, and positron emission tomography (PET)-CT data.

3. The ultrasound system of claim 1, wherein the processor compares values of pixels in the reference image with values of corresponding pixels in the ultrasound image, removes the ultrasound image if a brightness value difference between the reference image and the ultrasound image exceeds a preset threshold value, and sets the ultrasound image as an ultrasound image for producing the change information about the target object if the brightness value difference between the reference image and the ultrasound image is less than or equal to the preset threshold value.

4. The ultrasound system of claim 1, wherein the processor compares values of voxels in the reference image with values of corresponding voxels in the ultrasound image, removes the ultrasound image if a difference between voxels in the reference image and the ultrasound image exceeds a preset threshold value, and sets the ultrasound image as an ultrasound image for producing the change information about the target object if the difference between voxels in the reference image and the ultrasound image is less than or equal to the preset threshold value.

5. The ultrasound system of claim 1, further comprising a user input interface configured to receive input information needed for setting a point on the target object in the reference image from a user.

6. The ultrasound system of claim 5, wherein the processor sets the point on the reference image based on the input information, performs edge detection on the reference image based on the point to detect an edge of the target object, sets a region of interest (ROI) corresponding to the target object on the reference image by using the detected edge, sets a point on the ultrasound image based on the point set on the reference image, performs edge detection on the ultrasound image based on the point set on the ultrasound image to detect an edge of the target object, and sets an ROI corresponding to the target object on the ultrasound image by using the detected edge.

7. The ultrasound system of claim 6, wherein the processor performs image comparison based on the ROIs.

8. The ultrasound system of claim 7, wherein the image comparison is performed using at least one of a differential image, an intensity change, a texture change, signal phase, and signal attenuation.

9. The ultrasound system of claim 7, wherein the processor performs the image comparison between a current ultrasound image and a previous ultrasound image.

10. The ultrasound system of claim 7, wherein the processor performs the image comparison among the reference image, a current ultrasound image, and a previous ultrasound image.

11. The ultrasound system of claim 10, wherein the processor produces the change information including an ROI corresponding to the target object in the reference image, an ROI corresponding to the target object in the previous ultrasound image, an ROI corresponding to the target object in the current ultrasound image, and information about a difference in size of the target object due to the RFA.

12. The ultrasound system of claim 11, wherein the ROI corresponding to the target object in the reference image, the ROI corresponding to the target object in the previous ultrasound image, and the ROI corresponding to the target object in the current ultrasound image have the same color as or different colors than one another.

13. The ultrasound system of claim 11, wherein the ROI corresponding to the target object in the reference image, the ROI corresponding to the target object in the previous ultrasound image, and the ROI corresponding to the target object in the current ultrasound image have the same shape as or different shapes than one another.

14. The ultrasound system of claim 11, wherein the information about a difference in size of the target object is represented as a number or graph.

15. The ultrasound system of claim 7, wherein the processor performs the image comparison among the reference image, a current ultrasound image, and a predetermined number of previous ultrasound images.

16. The ultrasound system of claim 15, wherein the processor produces the change information including an ROI corresponding to the target object in the reference image, an ROI corresponding to the target object in each of the predetermined number of previous ultrasound images, an ROI corresponding to the target object in the current ultrasound image, and information about a difference in size of the target object due to the RFA.

17. The ultrasound system of claim 16, wherein the ROI corresponding to the target object in the reference image, the ROI corresponding to the target object in each of the predetermined number of previous ultrasound images, and the ROI corresponding to the target object in the current ultrasound image have the same color as or different colors from one another.

18. The ultrasound system of claim 16, wherein the ROI corresponding to the target object in the reference image, the ROI corresponding to the target object in each of the predetermined number of previous ultrasound images, and the ROI corresponding to the target object in the current ultrasound image have the same shape as or different shapes from one another.

19. The ultrasound system of claim 16, wherein the information about a difference in size of the target object is represented as a number or graph.

20. The ultrasound system of claim 15, wherein the processor produces the change information including an ROI corresponding to the target object in the reference image, an ROI corresponding to the target object in the current ultrasound image, and a marker for indicating a portion that is subjected to the RFA in the current ultrasound image.

21. The ultrasound system of claim 1, further comprising a user input interface configured to receive input information needed for setting an edge region of the target object on the reference image as an ROI from a user.

22. The ultrasound system of claim 21, wherein the processor sets the ROI on the reference image based on the input information, performs edge detection on the ultrasound image based on the ROI set on the reference image to detect an edge of the target object, and sets an ROI corresponding to the target object on the ultrasound image by using the detected edge.

23. The ultrasound system of claim 1, wherein the ultrasound probe transmits an ultrasound signal to the living body and receives an ultrasound echo signal reflected from the living body to create a reception signal in a freehand manner.

24. A method of providing change information of a target object, the method comprising:
    transmitting an ultrasound signal to a living body containing the target object during radiofrequency ablation (RFA), receiving an ultrasound echo signal reflected from the living body to acquire ultrasound data, through an ultrasound probe, and detecting a three-dimensional (3D) position of the ultrasound probe to create a first 3D position information of the ultrasound probe;
    extracting image data of the living body acquired before undergoing the RFA from a storage and producing a reference image which has a second 3D position information obtained based on a 3D position of a living body;
    producing an ultrasound image by using the ultrasound data;
    performing image registration between the reference image and the ultrasound image based on the first 3D position information and the second 3D position information; and
    comparing the reference image and the ultrasound image that have undergone the image registration with each other and producing the change information indicative of a change in the target object;
    wherein the comparing of the reference image with the ultrasound image and the producing of the change information further comprises:
        comparing the reference image and a previous ultrasound image and producing a first change information about the target object;
        comparing the reference image and a current ultrasound image and producing a second change information about the target object; and
    comparing the first change information with the second change information and determining that an error occurs in the current ultrasound image, and
    wherein the comparing of the reference image with the ultrasound image and the producing of the change information further comprises:
        detecting a first size change in size of the target object in the reference image and in a previous ultrasound image;
        detecting a second size change in size of the target object in the reference image and in a current ultrasound image; and
        comparing the first size change with the second size change and, if a difference between the first and second size changes exceeds a preset threshold value, determining that an error occurs in the current ultrasound image and removing the current ultrasound image.

25. The method of claim 24, wherein the image data includes at least one of magnetic resonance imaging (MRI) data, computed tomography (CT) data, ultrasound data, and positron emission tomography (PET)-CT data.

26. The method of claim 24, wherein the detecting of the ultrasound image comprises:
    comparing values of pixels in the reference image with values of corresponding pixels in the ultrasound image;
    removing the ultrasound image if a brightness value difference between the reference image and the ultrasound image exceeds a preset threshold value; and
    setting the ultrasound image as an ultrasound image for producing the change information of the target object if the brightness value difference between the reference image and the ultrasound image is less than or equal to the preset threshold value.

27. The method of claim 24, wherein the detecting of the ultrasound image comprises:
    comparing values of voxels in the reference image with values of corresponding voxels in the ultrasound image;
    removing the ultrasound image if a difference between voxels in the reference image and the ultrasound image exceeds a preset threshold value;
    setting the ultrasound image as an ultrasound image for producing change information about the target object if the difference between voxels in the reference image and the ultrasound image is less than or equal to the preset threshold value.

28. The method of claim 24, wherein the comparing of the reference image with the ultrasound image and the producing of the change information further comprises receiving input information needed for setting a point on the target object in the reference image from a user.

29. The method of claim 28, wherein the comparing of the reference image with the ultrasound image and the producing of the change information comprises:
setting the point on the reference image based on the input information;
performing edge detection on the reference image based on the point to detect an edge of the target object;
setting a region of interest (ROI) corresponding to the target object on the reference image by using the detected edge;
setting a point on the ultrasound image based on the point set on the reference image;
performing edge detection on the ultrasound image based on the point set on the ultrasound image to detect an edge of the target object; and
setting an ROI corresponding to the target object on the ultrasound image by using the detected edge.

30. The method of claim 29, wherein the comparing of the reference image with the ultrasound image and the producing of the change information comprises performing image comparison based on the ROIs.

31. The method of claim 30, wherein the image comparison is performed using at least one of a differential image, an intensity change, a texture change, signal phase, and signal attenuation.

32. The method of claim 30, wherein the comparing of the reference image with the ultrasound image and the producing of the change information comprises performing the image comparison between a current ultrasound image and a previous ultrasound image.

33. The method of claim 30, wherein the comparing of the reference image with the ultrasound image and the producing of the change information comprises performing the image comparison among the reference image, a current ultrasound image, and a previous ultrasound image.

34. The method of claim 33, wherein the comparing of the reference image with the ultrasound image and the producing of the change information comprises producing the change information including an ROI corresponding to the target object in the reference image, an ROI corresponding to the target object in the previous ultrasound image, an ROI corresponding to the target object in the current ultrasound image, and information about a difference in size of the target object due to the RFA.

35. The method of claim 34, wherein the ROI corresponding to the target object in the reference image, the ROI corresponding to the target object in the previous ultrasound image, and the ROI corresponding to the target object in the current ultrasound image have the same color as or different colors than one another.

36. The method of claim 34, wherein the ROI corresponding to the target object in the reference image, the ROI corresponding to the target object in the previous ultrasound image, and the ROI corresponding to the target object in the current ultrasound image have the same shape as or different shapes than one another.

37. The method of claim 34, wherein the information about a difference in size of the target object is represented as a number or graph.

38. The method of claim 30, wherein the comparing of the reference image with the ultrasound image and the producing of the change information comprises performing the image comparison among the reference image, a current ultrasound image, and a predetermined number of previous ultrasound images.

39. The method of claim 38, wherein the comparing of the reference image with the ultrasound image and the producing of the change information comprises producing the change information including an ROI corresponding to the target object in the reference image, an ROI corresponding to the target object in each of the predetermined number of previous ultrasound images, an ROI corresponding to the target object in the current ultrasound image, and information about a difference in size of the target object due to the RFA.

40. The method of claim 39, wherein the ROI corresponding to the target object in the reference image, the ROI corresponding to the target object in each of the predetermined number of previous ultrasound images, and the ROI corresponding to the target object in the current ultrasound image have the same color as or different colors from one another.

41. The method of claim 39, wherein the ROI corresponding to the target object in the reference image, the ROI corresponding to the target object in each of the predetermined number of previous ultrasound images, and the ROI corresponding to the target object in the current ultrasound image have the same shape as or different shapes from one another.

42. The method of claim 39, wherein the information about a difference in size of the target object is represented as a number or graph.

43. The method of claim 38, wherein the comparing of the reference image with the ultrasound image and the producing of the change information comprises producing the change information including an ROI corresponding to the target object in the reference image, an ROI corresponding to the target object in the current ultrasound image, and a marker for indicating a portion that is subjected to the RFA in the current ultrasound image.

44. The method of claim 24, wherein the comparing of the reference image with the ultrasound image and the producing of the change information further comprises receiving input information needed for setting an edge region of the target object on the reference image as an ROI from a user.

45. The method of claim 44, wherein the comparing of the reference image with the ultrasound image and the producing of the change information comprises:
setting the ROI on the reference image based on the input information;
performing edge detection on the ultrasound image based on the ROI set on the reference image to detect an edge of the target object; and
setting an ROI corresponding to the target object on the ultrasound image by using the detected edge.

46. The method of claim 24, wherein the transmitting of an ultrasound signal to a living body and the receiving of an ultrasound echo signal to acquire ultrasound data comprises transmitting the ultrasound signal to the living body and receiving the ultrasound echo signal reflected from the living body in a freehand manner.

* * * * *